(12) United States Patent
Chen et al.

(10) Patent No.: US 11,627,899 B2
(45) Date of Patent: Apr. 18, 2023

(54) PUSH-TYPE BLOOD COLLECTION NEEDLE

(71) Applicant: Ningbo Medsun Medical Co., Ltd., Ningbo (CN)

(72) Inventors: Zhicheng Chen, Ningbo (CN); Chi Huang, Ningbo (CN)

(73) Assignee: NINGBO MEDSUN MEDICAL CO., LTD., Ningbo (CN)

( * ) Notice: Subject to any disclaimer, the term of this patent is extended or adjusted under 35 U.S.C. 154(b) by 0 days.

(21) Appl. No.: 16/465,815

(22) PCT Filed: Jan. 11, 2019

(86) PCT No.: PCT/CN2019/071345
§ 371 (c)(1),
(2) Date: May 31, 2019

(87) PCT Pub. No.: WO2020/077899
PCT Pub. Date: Apr. 23, 2020

(65) Prior Publication Data
US 2021/0228120 A1 Jul. 29, 2021

(30) Foreign Application Priority Data
Oct. 19, 2018 (CN) .......................... 201811221187.2

(51) Int. Cl.
*A61B 5/151* (2006.01)
*A61B 5/15* (2006.01)

(52) U.S. Cl.
CPC .... *A61B 5/15113* (2013.01); *A61B 5/150435* (2013.01); *A61B 5/150534* (2013.01)

(58) Field of Classification Search
CPC .......... A61B 5/15113; A61B 5/150435; A61B 5/150534; A61B 5/15111; A61B 5/150541; A61B 5/150049; A61B 5/15057; A61B 5/15126; A61B 5/15117; A61B 5/1513; A61B 5/15142; A61B 5/15144
USPC ........................................................ 600/576
See application file for complete search history.

(56) References Cited

U.S. PATENT DOCUMENTS

| 5,439,473 A * | 8/1995 | Jorgensen | A61B 5/15142 |
| | | | 604/136 |
| 8,118,825 B2 * | 2/2012 | Schraga | A61B 5/1513 |
| | | | 606/182 |
| 2007/0185516 A1 * | 8/2007 | Schosnig | A61B 5/15117 |
| | | | 606/181 |

FOREIGN PATENT DOCUMENTS

CN  201341887 Y  * 11/2009

* cited by examiner

*Primary Examiner* — Alex M Valvis
*Assistant Examiner* — Chanel J Jhin
(74) *Attorney, Agent, or Firm* — Dragon Sun Law Firm, PC; Jinggao Li; Nathaniel Perkins (57) ABSTRACT

A push-type blood collection needle includes a housing having an accommodating cavity therein, a rear cover and a needle body disposed in the accommodating cavity. The rear cover is movably disposed on the housing, and the rear cover has a supporting leg extending into the accommodating cavity. The needle body is provided with a rib. The accommodating cavity is internally provided with a projecting part that cooperates with and blocks the bottom of the rib. The supporting leg is provided with a stopper that cooperates with and blocks the side wall of the rib. And an elastic member is disposed between the needle body and the rear cover.

12 Claims, 10 Drawing Sheets

PUSH-TYPE BLOOD COLLECTION NEEDLE

FIELD OF THE INVENTION

The present invention relates to the technical field of medical instruments, in particular to a push-type blood collection needle.

DESCRIPTION OF THE PRIOR ART

In the clinical laboratories of the hospital and blood collection agencies, blood tests, chemical examinations and samplings are often performed, which all require to be done with blood collection needles. In the prior art, disposable blood collection needles are in various forms. The traditional blood collection needle generally consists of a needle and a needle handle. When using, the blood collection site is pressed, and the needle tip quickly pricks the skin and then is pulled out. The traditional blood collection method with a blood collection needle has higher requirements for users, and the depth of the prick cannot be strictly controlled in this method. And some blood collection needles on the market need to be assembled manually, which is very inefficient.

SUMMARY OF THE INVENTION

In view of the disadvantages and deficiencies of the prior art, the object of the present invention is to provide a push-type blood collection needle that can achieve automated assembly production, ensure safe blood collection and control the depth of the prick.

To achieve the above object, the present invention provides the following technical solutions: a push-type blood collection needle, comprising a housing having an accommodating cavity therein, a rear cover and a needle body disposed in the accommodating cavity. The rear cover is movably disposed on the housing, and the rear cover has a supporting leg (21) extending into the accommodating cavity. The needle body is provided with a rib. The accommodating cavity is internally provided with a projecting part that cooperates with and blocks the bottom of the rib.

The supporting leg is provided with a stopper that cooperates with and blocks the side wall of the rib. An elastic member is disposed between the needle body and the rear cover.

Further, the elastic member is a first spring.

Further, the elastic member is a part of the rear cover.

Further, a second spring is disposed between the needle body and the accommodating cavity.

Further, a lower end of the rib is provided with a first inclined surface, an upper end of the stopper is provided with a second inclined surface that cooperates with the first inclined surface, and the projecting part is provided with a third inclined surface that cooperates with the first inclined surface.

Further, a sliding slot is disposed in the accommodating cavity for engaging with the rib, and the sliding slot is located by a side of the stopper.

Further, the accommodating cavity is provided with a transition block between the stopper and the sliding slot, and the transition block is provided with a fourth inclined surface that cooperates with the first inclined surface.

Further, the transition block cooperates with the projecting part to form a guide groove that engages with the supporting leg.

Further, the number of the ribs is two, and the two ribs are circumferentially symmetrically distributed as a whole, and the number of the supporting legs and the number of the projecting parts are also two.

Further, an end of the housing connected to the rear cover extends inwardly with a stop ring, and the rear cover is provided with a limiting block that cooperates with the stop ring.

Further, the needle body includes a protective cap having brims that abuts against the housing to impede axial movement of the needle body.

Further, the needle body includes a protective cap having lugs, and the lugs have slopes for guiding the protective cap to disengage from the needle body.

The beneficial effects of the invention are: the blood collection needle of the invention consists only of the housing, the first spring, the second spring, the needle body and the rear cover, it can be produced by machine, has simple structure, can realize automatic assembly production, and liberate labor, when in use, the rear cover is pressed downward, and the first spring is compressed during the downward movement of the rear cover, so that the rear cover drives the supporting leg to move downward, and meanwhile the needle body moves the rib relative to the projecting part under the action of the first spring, when the stopper of the supporting leg moves below the rib and no longer abuts against the rib, the needle body continues to move the rib relative to the projecting part under the action of the first spring until the rib is separated from the projecting part, the projecting part no longer limits the needle body, and the needle body is shot forward under the action of the first spring to complete the prick action and realize the blood collection function.

In the FIGS: 10. housing; 11. accommodating cavity; 12. projecting part; 13. third inclined surface; 14. sliding slot; 15. transition block; 16. fourth inclined surface; 17. guide groove; 19. stop ring; 20. rear cover; 21. supporting leg; 22. stopper; 23. second inclined surface; 24. limiting block; 30. needle body; 31. rib; 32. first inclined surface; 33. protective cap; 331 & 332. brims; 341 & 342. lugs; 40. first spring; 50. second spring; 100. blood collection needle.

DETAILED DESCRIPTION OF THE PREFERRED EMBODIMENTS

The technical solutions of the present invention are further described below with reference to the drawings, but the present invention is not limited to these embodiments.

Figure 1:
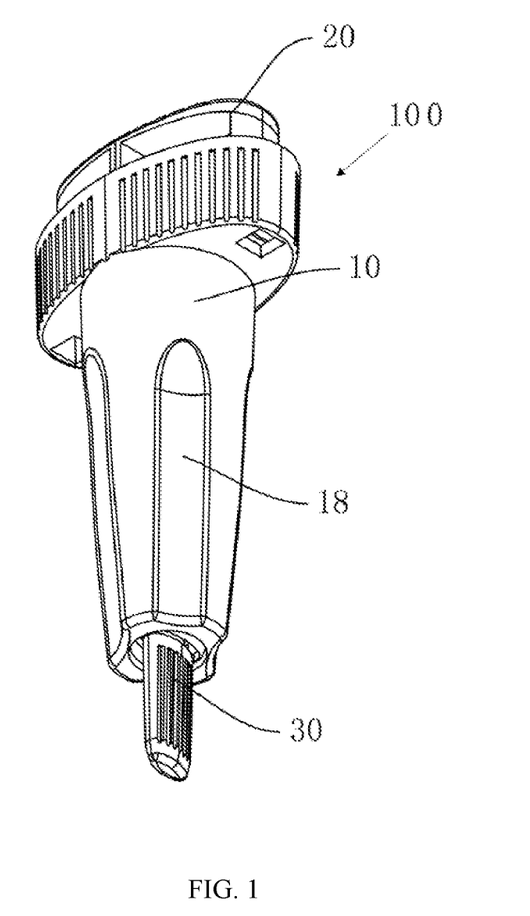
FIG. 1 is a schematic view of the overall structure of the present invention.
Figure 2:
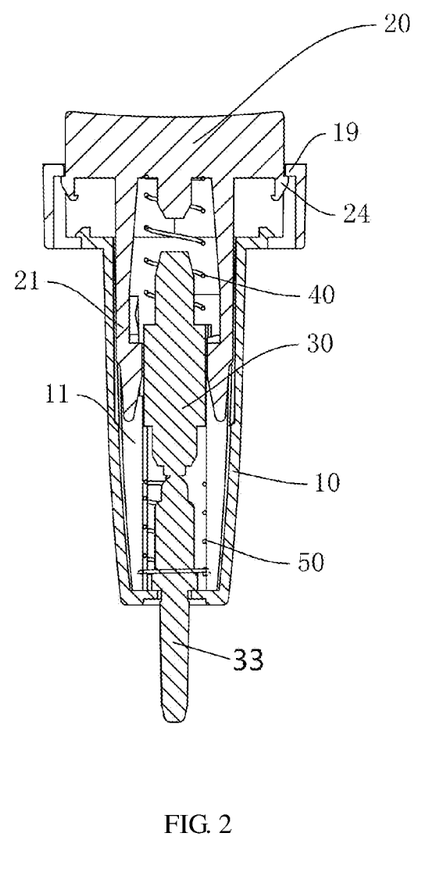
FIG. 2 is a cross section view of the present invention.
Figure 3:
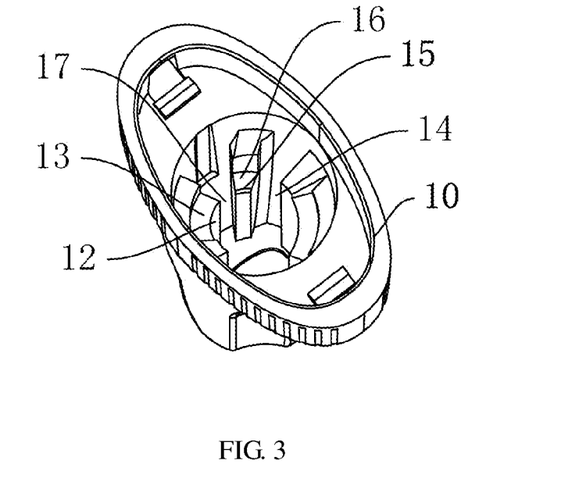
FIG. 3 is a schematic view of the structure of a housing of the present invention.
Figure 4:
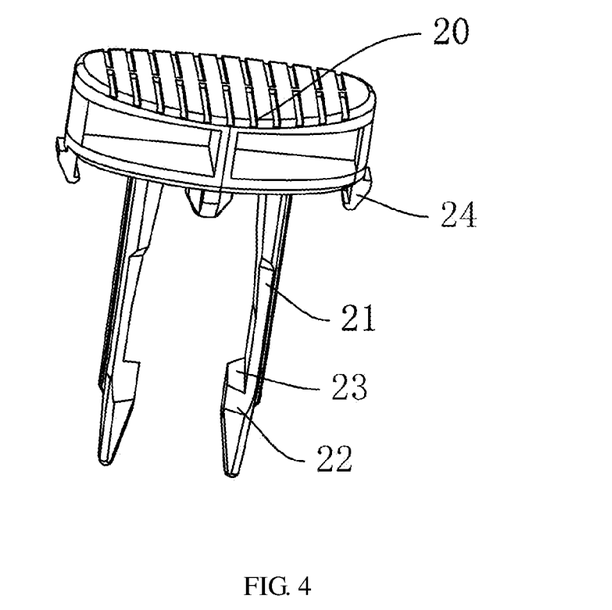
FIG. 4 is a schematic view of the structure of a rear cover of the present invention.
Figure 5:
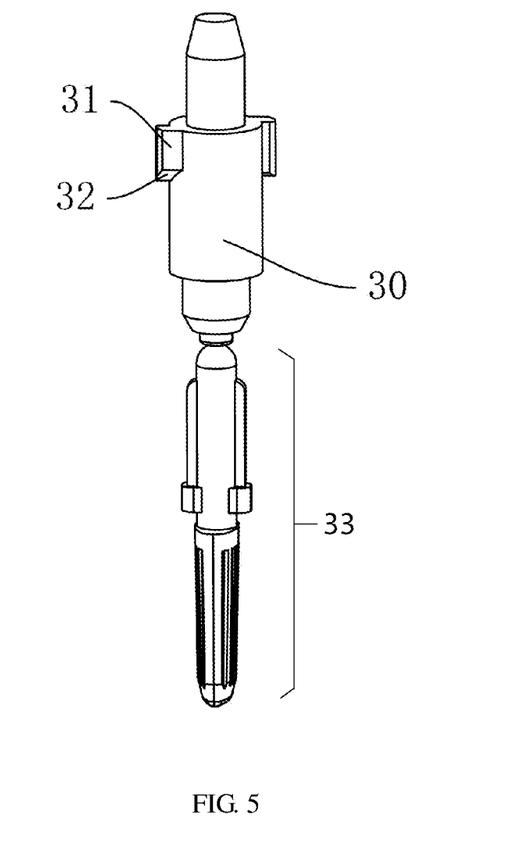
FIG. 5 is a schematic view of the structure of a needle body of the present invention.

As shown in FIGS. 1 to 5, a push-type blood collection needle 100 comprises a housing 10 having an accommodating cavity 11 therein, a rear cover 20 and a needle body 30 disposed in the accommodating cavity 11. The needle body 30 is provided with a protective cap 33. The protective cap 33 prevents the needle of the needle body 30 from being infected when not in use, and makes the blood collection needle 100 safer to use. The protective cap 33 is unscrewed before using to expose the metal needle, and then the rear cover 20 is pressed to collect blood. The rear cover 20 is movably disposed on the housing 10, and the rear cover 20 has a supporting leg 21 that extends into the accommodating cavity 11. The needle body 30 is provided with a rib 31, the accommodating cavity 11 is internally provided with a projecting part 12 that cooperates with and blocks the bottom of the rib 31. The supporting leg 21 is provided with a stopper 22 that cooperates with and blocks the side wall of the rib 31, and an elastic member is disposed between the needle body 30 and the rear cover 20. When the elastic member is in a compressed state, the needle body 30 has a tendency to move relative to the projecting part 12. The elastic member in this embodiment is the first spring 40. Besides, the elastic member may also be an elastic structure which is a part of the rear cover 20. A second spring 50 is disposed between the needle body 30 and the accommodating cavity 11. An end of the housing 10 connected to the rear cover 20 extends inwardly with a stop ring 19. The rear cover 20 is provided with a limiting block 24 that cooperates with the stop ring 19. A slope is provided on the side wall of the limiting block 24 such that it is more convenient for the rear cover 20 to reach into the housing 10. The upper end of the limiting block 24 is provided with a plane. When the rear cover 20 reaches into the housing 10, the first spring 40 abuts against the rear cover 20, so that the plane of the upper end of the limiting block 24 abuts against the stop ring 19 of the housing 10, thereby preventing the rear cover 20 from being detached from the inside of the housing 10. A plurality of concave surfaces 18 are provided on the outer wall of the housing 10, so that the user can hold the housing 10 more firmly.

The blood collection needle 100 of the present invention consists only of the housing 10, the first spring 40, the second spring 50, the needle body 30 and the rear cover 20. It can be produced by machine, has simple structure, can realize automatic assembly production, and liberate labor. When in use, the rear cover 20 is pressed downward, and the first spring 40 is compressed during the downward movement of the rear cover 20, so that the rear cover 20 drives the supporting leg 21 to move downward, and meanwhile the needle body 30 moves the rib 31 relative to the projecting part 12 under the action of the first spring 40. When the stopper 22 of the supporting leg 21 moves below the rib 31 and no longer abuts against the rib 31, the needle body 30 continues to move the rib 31 relative to the projecting part 12 under the action of the first spring 40 until the rib 31 is separated from the projecting part 12. The projecting part 12 no longer limits the needle body 30, and the needle body 30 is shot forward under the action of the first spring 40 to complete the prick action and realize the blood collection function. At the same time, the needle body 30 will abut against the second spring 50 during the forward shot and compress the second spring 50. The force applied by the second spring 50 to the needle body 30 is opposite to the force applied by the first spring 40 to the needle body 30. Therefore, the second spring 50 cooperates with the first spring 40 to control the depth at which the skin is pricked by the needle body 30, thereby avoiding a situation where it is too deep or too shallow. Moreover, after the blood collection is completed, the second spring 50 provides an elastic force to retract the needle body 30 to the housing 10, thereby preventing the needle of the needle body 30 from being exposed to cause stab wounds or even infection, and blood collection is safer. In this embodiment, the number of the ribs 31 is two, and the two ribs 31 are circumferentially symmetrically distributed as a whole, and the numbers of the supporting legs 21 and the projecting parts 12 are also correspondingly two, so that the stability of the integral structure is better.

Further, the lower end of the rib 31 is provided with a first inclined surface 32, and the upper end of the stopper 22 is provided with a second inclined surface 23 cooperated with the first inclined surface 32, and the projecting part 12 is provided with a third inclined surface 13 cooperated with the first inclined surface 32. When the first spring 40 is pressed by the rear cover 20, the first inclined surface 32 and the third inclined surface 13 are in contact with each other, thereby facilitating the movement of the rib 31 relative to the projecting part 12. Moreover, the upper end of the block 22 is provided with the second inclined surface 23 which cooperates with the first inclined surface 32. The rear cover 20 drives the supporting leg 21. When the upper end surface of the stopper 22 of the supporting leg 21 is moved to be align with the third inclined surface 13 of the projecting part 12, the stopper 22 is no longer block the rib 31, and the rib 31 is moved along the third inclined surface 13 to the upper end surface of the stopper 22. At this time, the first inclined surface 32 of the rib 31 is in contact with the second inclined surface 23, so that the rib 31 is moved relative to the stopper 22. When the rib 31 moves out of the stopper 22, the rib 31 is no longer restrained by the stopper 22, and the needle 30 is shot forward by the action of the first spring 40 to complete the prick action. The accommodating cavity 11 is internally provided with a sliding slot 14 for engaging with the rib 31. The sliding slot 14 is located by the side of the stopper 22. The accommodating cavity 11 is internally provided with a transition block 15 between the stopper 22 and the sliding slot 14. The transition block 15 is provided with a fourth inclined surface 16 that cooperates with the first inclined surface 32. When the rib 31 moves out of the stopper 22, the rib 31 moves to the transition block 15. The transition block 15 is provided with a fourth inclined surface 16 that cooperates with the first inclined surface 32. At this time, the first inclined surface 32 of the rib 31 is in contact with the second inclined surface 23, so that the rib 31 is moved relative to the transition block 15. The accommodating cavity 11 is internally provided with a sliding slot 14 which cooperates with the rib 31. When the rib 31 moves out of the transition block 15, the rib 31 moves into the sliding slot 14, and then moves forward along the sliding slot 14, so that the needle body 30 is shot forward to complete the prick action. When the needle body 30 moves relative to the housing 10, the rib 31 moves in the sliding slot 14. The sliding slot 14 defines and guides the movement direction of the rib 31. It has a clear trajectory and a simple structure, and plays a role in stabilizing the structure. A guide groove 17 that engages with the supporting leg 21 is formed between the transition block 15 and the projecting part 12. When the rear cover 20 is pressed, the supporting leg 21 of the rear cover 20 moves in the guide groove 17. The guide groove 17 defines and guides the movement direction of the supporting leg 21. It has a clear trajectory and a simple structure, and plays a role in stabilizing the structure to prevent the rear cover 20 from rotating relative to the housing 10.

Figure 6:
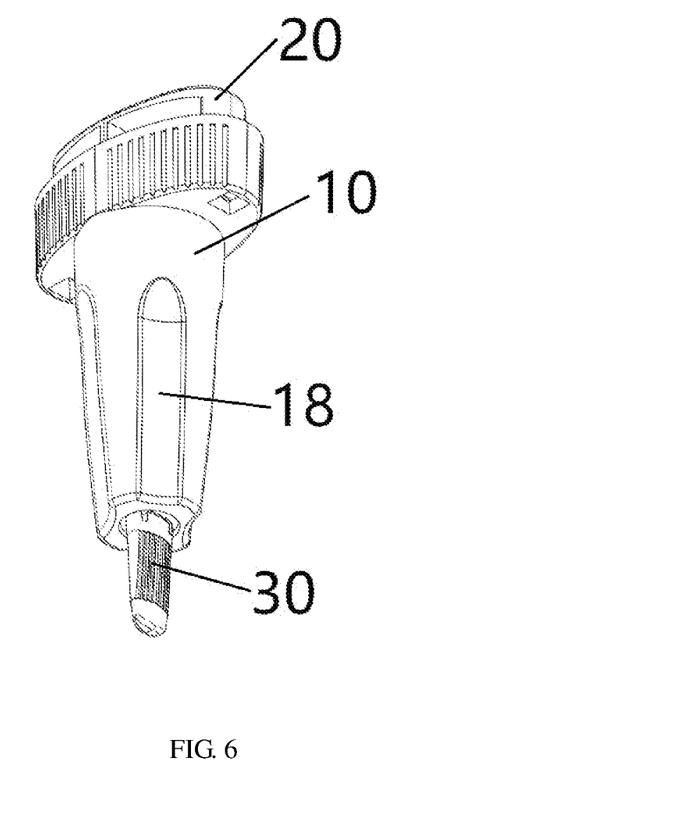
FIG. 6 is a schematic view of the overall appearance structure of another preferred embodiment of the present invention.
Figure 7:
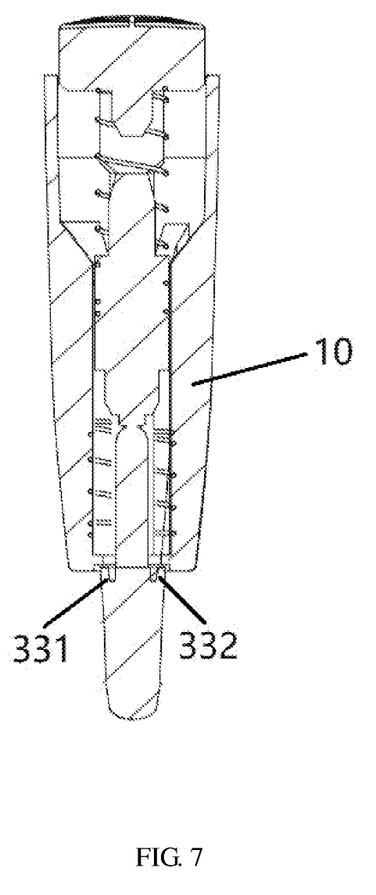
FIG. 7 is a cross section view of another preferred embodiment of the present invention.
Figure 8:
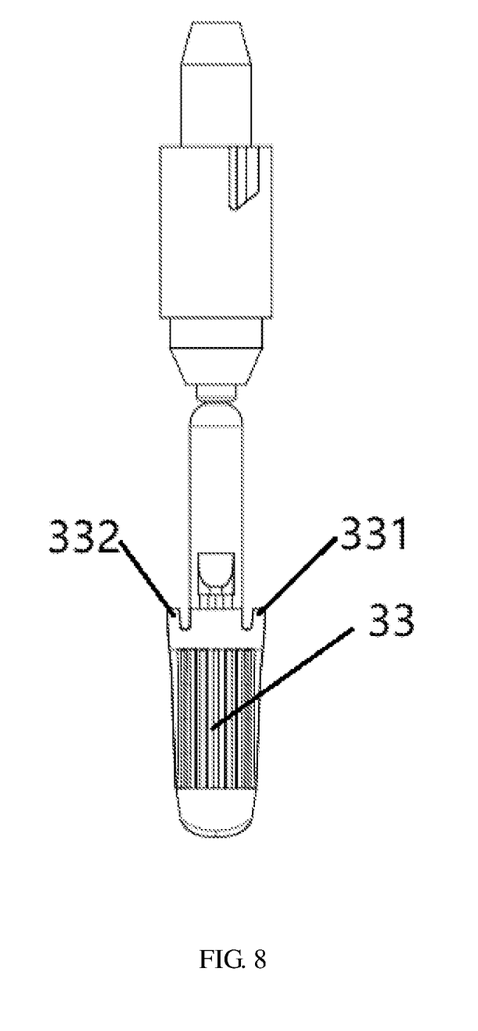
FIG. 8 is a front view of a needle body of another preferred embodiment of the present invention.
Figure 9:
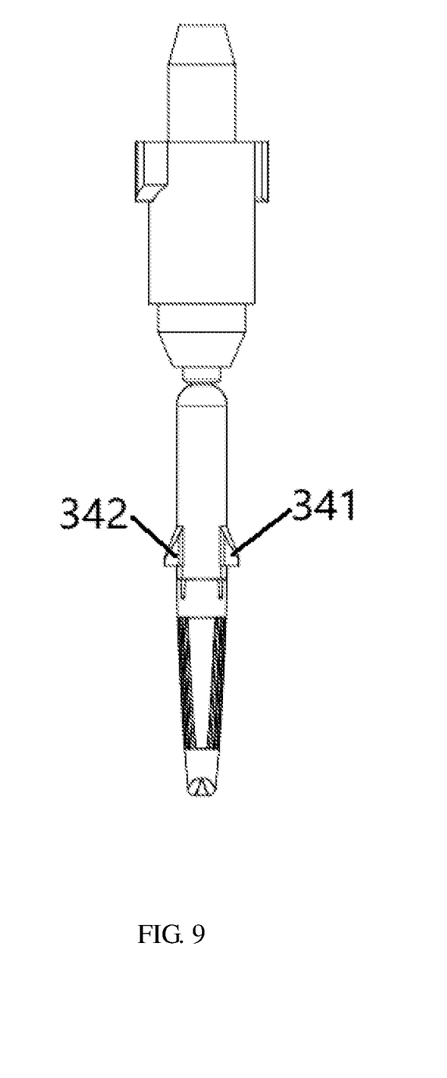
FIG. 9 is a side view of a needle body of another preferred embodiment of the present invention.
Figure 10:
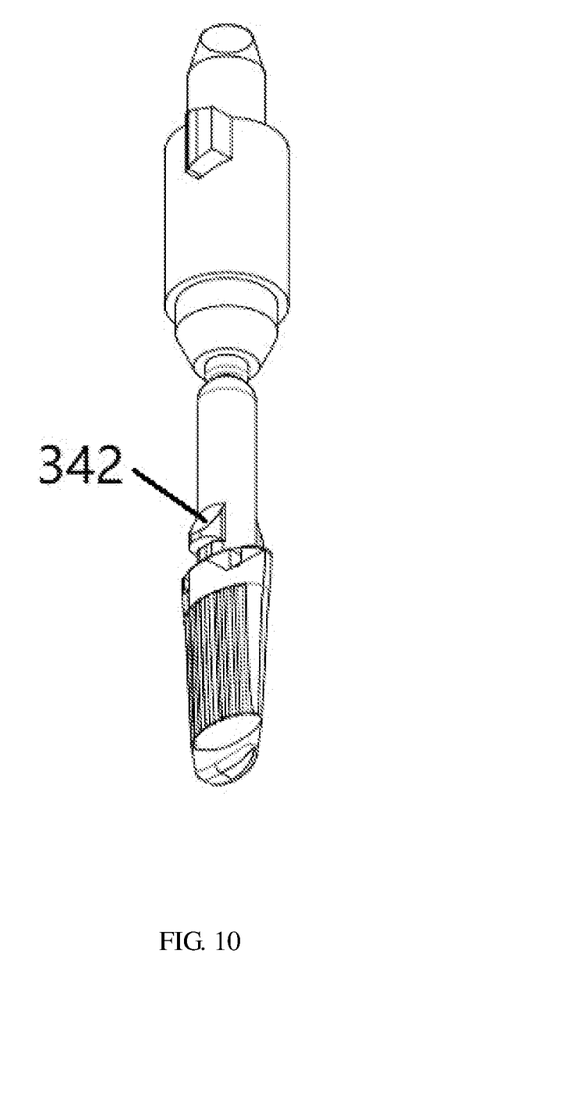
FIG. 10 is a perspective view of a needle body of another preferred embodiment of the present invention.
Figure 11:
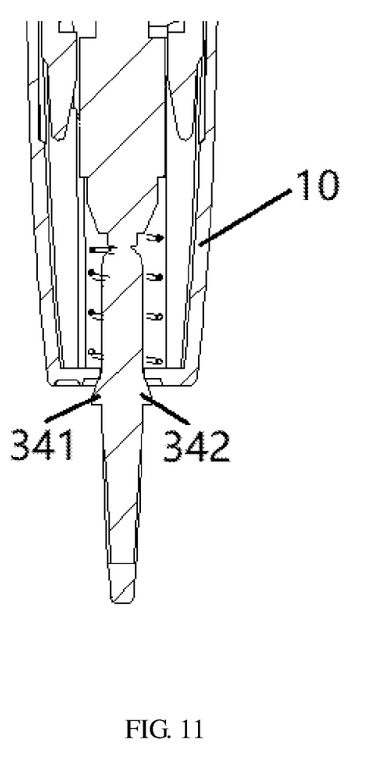
FIG. 11 is a cross section view of another preferred embodiment of the present invention.

FIGS. 6-11 is another embodiment of the present invention, with only the portion of the needle body 30 being modified, the rest remaining identical to the embodiment described above. In this embodiment, the protective cap 33 of the needle body 30 has brims 331 and 332. When the protective cap 33 is turned, the brims 331 and 332 will abut against the housing 10, thereby offsetting the axial force occurring, and avoiding the axial retraction or skew of the needle body 30 which will cause the needle body 30 to fail when the rear cover 20 is pressed. In addition, the protective cap 30 in this embodiment further includes lugs 341 and 342. The lugs 341 and 342 have slopes which are in contact with the housing 10. When the protective cap 33 is turned, the slopes serve to guide the pulling out of the protective cap 33 and prevent the needle body 30 from retreating, so that it is more labor-saving and stable when the protective cap 33 is disengaged from the needle body 30.

The particular embodiments described herein are merely illustrative of the spirit of the present invention. A person skilled in the art can make various modifications or additions to the particular embodiments described or replace them in a similar manner, without departing from the spirit of the present invention or beyond the scope of the appended claims.

The invention claimed is:

1. A push-type blood collection needle, comprising a housing having an accommodating cavity therein, a rear cover and a needle body disposed in the accommodating cavity, wherein the rear cover is movably disposed on the housing, the rear cover has a supporting leg extending into the accommodating cavity, the needle body is provided with a rib, the accommodating cavity is internally provided with a projecting part that cooperates with and blocks the bottom of the rib, the supporting leg is provided with a stopper that cooperates with and blocks the side wall of the rib, and an elastic member is disposed between the needle body and the rear cover; wherein the push-type blood collection needle is configured that after the rear cover is pressed downward, the needle body moves the rib relative to the projecting part under an action of the elastic member, and after the stopper of the supporting leg moves below the rib and no longer abuts against the rib, the needle body continues to move the rib relative to the projecting part under the action of the elastic member until the rib is separated from the projecting part.

2. The push-type blood collection needle according to claim 1, wherein said elastic member is a first spring.

3. The push-type blood collection needle according to claim 1, wherein said elastic member is a part of the rear cover.

4. The push-type blood collection needle according to claim 1, wherein a second spring is disposed between the needle body and the accommodating cavity.

5. The push-type blood collection needle according to claim 1, wherein a lower end of the rib is provided with a first inclined surface, an upper end surface of the stopper is provided with a second inclined surface that cooperates with the first inclined surface, and an upper end surface of the projecting part is a third inclined surface that cooperates with the first inclined surface; wherein the push-type blood collection needle is configured that after the rear cover is pressed downward, the first inclined surface and the third inclined surface are in contact with each other, thereby facilitating a movement of the rib relative to the projecting part, and when the upper end surface of the stopper is moved to be flush with the projecting part, the rib is moved along the third inclined surface to the upper end surface of the stopper, then the first inclined surface is in contact with the second inclined surface, so that the rib is moved relative to the stopper.

6. The push-type blood collection needle according to claim 5, wherein a sliding slot is disposed in the accommodating cavity for engaging with the rib, and the sliding slot is located near the stopper.

7. The push-type blood collection needle according to claim 6, wherein the accommodating cavity is provided with a transition block between the stopper and the sliding slot, and the transition block is provided with a fourth inclined surface that cooperates with the first inclined surface.

8. The push-type blood collection needle according to claim 7, wherein the transition block cooperates with the projecting part to form a guide groove that engages with the supporting leg.

9. The push-type blood collection needle according to claim 1, wherein the number of the ribs is two, and the two ribs are circumferentially symmetrically distributed as a whole, and the number of the supporting legs and the number of the projecting parts are also two.

10. The push-type blood collection needle according to claim 1, wherein an end of the housing connected to the rear cover extends inwardly with a stop ring, and the rear cover is provided with a limiting block that cooperates with the stop ring.

11. The push-type blood collection needle according to claim 1, wherein the needle body includes a protective cap having brims that abut against the housing to impede axial movement of the needle body.

12. The push-type blood collection needle according to claim 1, wherein the needle body includes a protective cap having lugs, and the lugs have slopes for guiding the protective cap to disengage from the needle body.

* * * * *